United States Patent
Van der Zel

(10) Patent No.: US 6,495,072 B1
(45) Date of Patent: Dec. 17, 2002

(54) METHOD FOR MAKING BASIS FOR A DENTAL RESTORATION

(75) Inventor: Joseph Maria Van der Zel, Hoorn (NL)

(73) Assignee: Cicero Dental Systems B.V. (NL)

(*) Notice: Subject to any disclaimer, the term of this patent is extended or adjusted under 35 U.S.C. 154(b) by 0 days.

(21) Appl. No.: 09/497,396

(22) Filed: Feb. 3, 2000

(30) Foreign Application Priority Data

Feb. 5, 1999 (NL) .............................................. 1011218
Mar. 24, 1999 (NL) .............................................. 1011659

(51) Int. Cl.$^7$ .............................................. A61C 13/00
(52) U.S. Cl. ........................ 264/16; 264/643; 264/671; 264/678; 264/125
(58) Field of Search ............................ 264/19, 16, 643, 264/642, 671, 672, 673, 125, 678

(56) References Cited

U.S. PATENT DOCUMENTS

| | | | |
|---|---|---|---|
| 4,265,669 A | | 5/1981 | Starling et al. |
| 4,772,436 A | * | 9/1988 | Tyszblat ....................... 264/19 |
| 5,565,152 A | * | 10/1996 | Oden et al. .................... 164/19 |
| 5,910,273 A | * | 6/1999 | Thiel et al. ..................... 264/16 |
| 6,106,747 A | * | 8/2000 | Wohlwend ..................... 264/16 |

FOREIGN PATENT DOCUMENTS

| | | | |
|---|---|---|---|
| EP | A-0241384 | 10/1987 | ............ A61C/5/10 |
| WO | WO 97/45377 | 12/1997 | ............ C03C/8/02 |

* cited by examiner

Primary Examiner—Christopher A. Fiorilla
(74) Attorney, Agent, or Firm—Mark Zovko

(57) ABSTRACT

A method for producing a ceramic material, subsequently including mixing ceramic material, such as oxidic ceramic material, which as a raw material essentially comprises aluminum oxide, zircon oxide and/or titanium oxide, and glass component; melting at least the glass component in the mixture by sintering, where the glass component infiltrates the ceramic material and absorbs raw material of the ceramic material through a reaction at the surface; and bringing the mixture into a shape, such as powder, which is suitable for further processing, such as additional sintering.

Also, a basis for the crown, the crown in its entirety having layers of for instance porcelain applied to the basis, and methods for producing the basis and the crown through subsequent processing steps, to which the basis is preferably subjected on the same underground, for instance based on CAD/CAM techniques.

13 Claims, 2 Drawing Sheets

METHOD FOR MAKING BASIS FOR A DENTAL RESTORATION

The present invention relates to a method for producing ceramic material, said ceramic material itself, a basis for a dental restoration, which is made from said ceramic material, and the method for production thereof, and a dental restoration with said basis and a method for producing said dental restoration.

For ceramic materials often aluminum oxide and/or zirconium oxide is used, i.e. oxidic ceramic. When producing dental restorations, such as crowns, it is known to use ceramic material as a basis therefore in the place of for instance metal, that remains visible after applying cover layers, for instance of porcelain. Ceramic material is preferred, because this results in a better esthetic appearance of the dental restoration to be produced, than metal. The basis of a dental restoration is placed on for instance the remains of a tooth, i.e. a tooth stump, and as such forms the basis or carrier of a dental restoration. In connection with the considerable dental forces, to which the dental restoration is subjected, the basis therefor needs to have a sufficient strength, apart from the visually observable properties in connection with the cover layers to be applied to the basis and made from e.g. porcelain to obtain the aforementioned esthetic effect. Moreover ceramic material is more desirable than metal because of the higher biocompatibility thereof.

Several ceramic materials, especially for the basis of a dental restoration, and methods for producing the ceramic material, the basis and the dental restoration are respectively known.

The American U.S. Pat. No. 5,104,319 relates to flame spraying the ceramic material, which in essence comprises aluminum oxide, zirconium oxide, titanium oxide or combination thereof to produce the basis for especially a dental restoration. Here ceramic material in powder form is suspended in a carrier liquid and subjected to a flame spraying process on an underground, having the form of a dental remain, e.g. the form of a tooth stump. According to this method small quantities of material, which is based on silicate, are added to increase the density, which corresponds to the strength of the basis of ceramic material. The strength, which can be obtained is however insufficient in order to apply the ceramic material and the method, when producing the basis of a dental restoration. The density, which is achieved, is too low for this, and the corresponding porousness is too high, such that tear formation, leading to fracture, can occur. As a matter of fact, this porousness of especially the grains of the raw material for the ceramic material is most sensitive for the enormous dental forces, occurring when used as a dental restoration, and can lead to tear formation and fracture, although the tensions in the basis as a whole remain below the desired fracture strength.

Another known technique is the use of massive dental porcelain to produce the entire dental restoration. This however has for a drawback, that this material is hard to process in order to realize the occlusal surfaces accurately as a result of the hardness of this dental porcelain. When the obtained form of the dental restoration is less than optimum, and the restoration inhibits free movement of the jaw, this can lead to occlusal discrepancies and dislocation of the cranio mandibular complex. Therefore, when placing such restorations, often corrections have to be made in order to avoid this problem, which is inhibited by the hardness of dental porcelain. Furthermore this dental porcelain exhibits a high degree of shrink during baking, as a result of which the fit on the underground and therefore later upon the dental remains is unsure and can even vary as a result of variations in the degree of shrink. A bad fit can lead to the dental restoration coming loose or disturbance of the cranio mandibular complex. Further the use of a uniform colored block leads to a restoration with an appearance, which seems considerably less lifelike.

Also essentially pure aluminum oxide can be pressed dry and sintered. However, to obtain a desirable appearance of the restoration addition of pigments is necessary, which disrupt the sintering process. Therefore products based on this known technology have an insufficient strength, when pigments are applied, or an insufficiently natural appearance.

Another known technique is for instance pressing the ceramic material dry onto the underground to form a basis, sintering the material and process it to the desired shape, for instance by milling. The application of ceramic material is for instance by pressing it in a dry form. The ceramic material as raw material essentially comprises aluminum oxide, zirconium oxide and/or titanium oxide or mixtures thereof. These ceramic materials and methods have for a disadvantage, that a considerable and largely unpredictable shrink occurs when sintering or baking. Furthermore the strength of the used ceramic materials is insufficient, in particular for application as a basis for a dental restoration. Also here the porousness of the grains of the powder of the raw materials for the ceramic material is the cause. Moreover the variation in the degree of shrink, which is anticipated by oversize production with an average shrink as a starting point, leads to inaccuracy of the fit and therefore losses in production through rejection of individual products with an incorrect fit. Deviating fit is however only to be detected, after the underground is removed. This inhibits continuous automated production processes, where this underground could be used to be engaged by a processing machine, such as a mill. As certainty about the fit first has to be obtained, the underground, however, needs to be removed. Also for applying the cover layers on the basis for the dental restoration, this necessity to remove the underground is an inhibition.

With the invention it is intended to remedy the problems and disadvantages of all the above mentioned techniques, to which end a method is provided for production of ceramic material, and the ceramic material itself is provided. The ceramic material, that results from the method according to the present application can be used in production of the basis for a dental restoration and therefore in production of the dental restoration itself, but can also be used as a substitute for plastic filling material, which is for instance used to fill cavities. By the absorption of raw material of the ceramic material the glass component is strengthened, where the glass component also infiltrates the porous structure of the ceramic material. Through this process a substantially massive mass is obtained without any porousness, because of which the strength of the products produced with this ceramic material, such as the basis for a dental restoration, exhibit a sufficient strength. The glass component also adheres to grains of the ceramic material, which is for instance in a powder form, so that these grains are among themselves connected by the glass component. As such a massive product is formed, which through supplemental sintering for producing the basis for a dental restoration, is powdered. This can be achieved by grinding. When thereafter this powder is applied to an underground, corresponding to a tooth stump, in an arbitrary manner, by spraying, brushing, or otherwise, the glass component becomes fluid and fluid phase sintering occurs. As a result the shrink when baking the ceramic material while sintering this ceramic material to form for instance the basis for a dental restoration, is overcome by the glass component and the basis securely fits exactly on the underground, where the underground has a shape corresponding exactly to that of the form of the tooth stump. This certainty obviates the need to remove the underground in order to verify the fit, so that the underground can remain in the basis during subsequent processing steps.

The underground is often made from an oven proof material, to which the ceramic material of the basis for a dental restoration adheres. Preferably this oven proof underground can be formed from partially sintered, or chemically bound aluminum oxide and/or zirconium oxide or mixtures thereof in order to ensure, that the basis adheres well thereto. By subsequently removing the underground in a milling manner, it is secured, that the restoration will fit well, so that passages along the sides and further dental decay and cavities under the influence of bacteria will not occur. The ceramic material according to the present invention can, in comparison with known techniques, be sintered very fast, whereby the production process of the actual basis or the dental restoration as a whole is accelerated.

These and other advantages and features of the present invention will be made clear from the subsequent description, which has been drawn up in correspondence with the drawings, in which.

Figure 1:
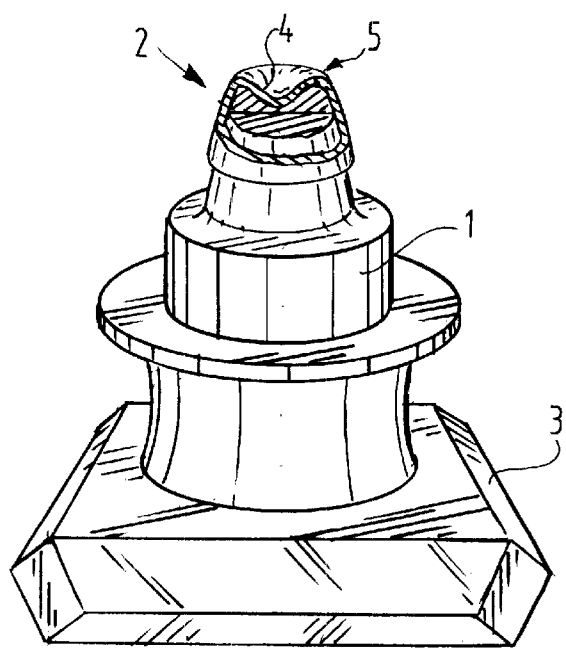
FIG. 1 shows a basis for a crown on an underground, made from ceramic material according to the present invention.

The ceramic material is produced, according to the present application, by mixing aluminum oxide, zircon oxide and/or titanium oxide, or mixtures thereof, with glass frit, of which the composition is described hereinbelow in more detail. Also other oxidic ceramics for sintering, other than aluminum oxide, zirconium oxide or titanium oxide be applied as well as other kinds of glass components, where the process parameters described hereinbelow, such as temperature, duration of the process, etc., are to be adapted to the properties of the materials used.

The powdered oxidic ceramic for sintering in the form of a powder and the glass component in the form of a powder are heated up to a temperature, where at least the glass component is sintered or melts to form a homogenous plate, together with the oxidic ceramic for sintering, such as aluminum oxide and/or zirconium oxide. The temperature during sintering is preferably between 1100 and 1200° C., dependent upon the used ceramic for sintering and the used glass component, and the time, during which the mixture is sintered, is approximately 24 hours.

During the process a surface reaction occurs between the grains of the oxidic ceramic for sintering and the surrounding glass, where a part of these compounds, especially aluminum oxide or zirconium oxide, diffuses into the glass phase, otherwise called the glass component.

The glass component is then strengthened by absorption of aluminum oxide, zirconium oxide and/or titanium oxide or any other oxidic ceramic material for sintering used. Then crystals are formed in the glass component and the glass component is strengthened.

Simultaneously the glass component infiltrates the grains of the powdered oxidic ceramic material for sintering entirely. This is enhanced by the relatively long duration for sintering. If desired the sintering process can be performed in a vacuum to enhance infiltration further.

Simultaneously the glass component virtually forms a coating over the grains of the powdered ceramic material for sintering during the sintering process, as a result of which these grains are interconnected by the glass component, which is strengthened by the formation of crystals therein. Therefore a solid body, for instance a plate, is formed, which can be cooled down after completion of the sintering process. This cooling down can be forced by dipping this plate in cooling water with a temperature of for instance 20° C., through which the formation of crystals is enhanced further.

Subsequently the product formed in this way is ground during a long period to form a fine powder. In order to achieve a sufficient fineness, the material can for instance be ground during up to 8 hours. The powdered ceramic material formed in this way can be used to produce a cap-like basis for a dental restoration, such as a crown.

If desired, quantities of metal oxides and/or pigments can be added to the powder. The natural appearance of a tooth can be simulated in the crown with pigments, especially when on the basis, formed as cap 5, of the crown transparent layers 6, 7, possibly colored materials themselves, such as porcelain, are applied. By using layered, possibly even colored porcelain, a very natural looking crown or restoration can be obtained, which will have the required strength as a result of the basis formed as cap 5 from the ceramic material according to the present invention. Here the oxidic ceramic material for sintering, intended for the basis formed as cap 5, which is in itself fragile, is strengthened because of the method according to the present invention.

In FIG. 1 an underground 1 is shown. The underground 1 is produced from ceramic and oven proof material. The underground is made from oven proof material in order to withstand the sintering process for the ceramic material according to the present invention.

The top 2 of the underground 1 has the shape for the carrier, for instance a tooth stump, for the dental restoration. For this an imprint is made from the jaw with the previously prepared tooth stump, which will be the carrier for the dental restoration to be produced. The imprint is cast in plaster. The obtained plaster model is scanned and input into a computer with the aid of a digital camera. For this the bottom part of the plaster model is painted black to mark in this way the bottom edge of the crown to be produced. When scanning the plaster model a fast laser line scanning method can for instance be used, where the three dimensional geometry of the plaster model of the preparation (the tooth stump) and the immediately adjacent dental elements can be determined. For this use can be made of a CCD camera to detect the lines projected by the laser.

Optionally the step of forming a plaster model could be omitted, when the three dimensional form of the tooth stump could be determined directly in the mouth.

The digital information on the three dimensional shape and geometry of the tooth stump for the dental restoration is input into a computer. If desired information can be added on the exact bottom edge of the crown or restoration to be produced, the separation surfaces with the neighboring dental elements, the saddle point of the restoration to be formed, etc. From this information the orientation of the occlusal plane can be determined. Within the parameters thus given or detected in relation to the shape and the geometry of the restoration to be produced, a choice can be made from a number of standard shapes, or information on the shape or geometry of the original tooth can be used, when such information is available. Also an opposite dental element can be chosen from an opposite line of teeth, where this opposite tooth can be scanned and used as a starting point in forming the restoration. These latter aspects naturally relate to the external shape of the restoration to be produced, while the shape of the tooth stump or carrier for the restoration or the crown determines the internal surface thereof.

If desired, the eventual shape of the restoration can be visualized with a computer simulation in connected with the neighboring dental elements in order to secure the fit thereof beforehand. The eventual shape of the restoration to be produced can then still be adjusted, based on gnathological rules. Here the shape of the restoration to be produced is adjusted to obtain an optimal tooth on tooth contact with the neighboring, as well as the opposite dental elements or teeth. Here jaw movements can be taken into account, and not only the static relationship between the restoration and the neighboring or opposite dental elements. During essentially three dimensional chewing movements maintaining the normal functioning is required, without interference of protrusions, which do not belong, and the chewing movements could be disturbed thereby with clear consequences, such as trauma to the jaws and unequal division of the load over the dental elements.

In order to disrupt the normal functioning of the dental system, for which the dental restoration is intended, as little as possible, measurements can be made to the dental system involved, i.e. the chewing movements which a patient actually makes, can be involved. For this an axiographic registration computer can for instance be used.

With the steps above the inner surface of the restoration for connection to the tooth stump, and the outer surface thereof are determined optimally. For the inner surface a thin layer of adhesive is taken into account.

With a processing machine, such as a mill under control of a CAD/CAM program a block of oven proof material is processed on the basis of the information obtained on the inner surface of the restoration to be produced to obtain the underground 1 with the top 2 thereof by machining a block of oven proof material. The top 2 then exactly has the shape of the dental remains or the tooth stump, on which the restoration is to be placed. At the side of the underground 1 opposite the top 2 a double-prismatic foot 3 is provided, which has a shape, that is standardized for a processing machine, such as the above mentioned mill. The foot 3 of the underground 1 can, in subsequent processing steps also function as a clamping element for processing machines, particularly mills.

The material of the underground 1 can be partially sintered aluminum oxide or zirconium oxide, dependent upon the expansion of the ceramic material to be applied according to the present invention. This will have to be machined away in a later stage. As an alternative chemically bound aluminum oxide and/or zircon oxide can be used. This can be dissolved chemically in a later stage. The chemical binding material can comprise a combination of magnesium oxide and ammonium monophosphate and a mixing fluid, comprising colloidal silicon oxide, aluminum oxide or zirconium oxide. The linear thermal expansion of the material for the underground 1 is tuned to that of the layer or layers of ceramic material to be applied according to the present invention. For illustrative purposes only it is noted here, that the expansion of pure aluminum is 7.8 $\mu$m/m.K (measured between 20 and 500° C.), and that the expansion coefficient of zircon oxide is 10.5 $\mu$m/m.K.

With these materials for the underground 1 a desired adhesion of the ceramic material according to the present invention is obtained, as will be described in more detail below.

The underground 1, and particularly the top 2 thereof, are accurately machined to the shape of the dental remains or the tooth stump, with a mill comprising a cylindrical disc and/or a round hard metal mill.

On the top 2 a layer 4 of the ceramic material according to the present invention is applied. This can be achieved in several ways, such as pressing dry material, isostatic press, spraying, or any other arbitrary way, where some degree of compression is desirable. Hereafter the layer 4 is sintered. During this process baking shrink of the ceramic material according to the present invention occurs, but because the glass component therein flows, as it were, this shrink is taken into account and compensated for, without having to take this shrink into account in order to obtain the desired fit, such as was the case with certain known techniques.

After sintering the cap 5 is formed. This cap 5 is the basis for the dental restoration to be produced. The cap 5 is adhered to the top 2 as a result of the choice of material for the oven proof underground 1. After this the foot 3 can be put back in the clamp of a mill (not shown) to machine the cap 5 back to the desired dimensions. These dimensions, particularly the thickness thereof, can also have been determined with the above mentioned CAD/CAM techniques in the step of forming a model of the dental restoration.

If desired sintering is completed in two steps; each one of these steps is then followed by a machining process, such as milling. In the first step the material is sintered at a relatively low temperature between 800 and 1000° C. during between 5 and 15 minutes in vacuum, where formation of a connection between the grains occurs, without the material compressing excessively. Hereinafter the cap 5 is subjected to a first milling process. As the material has not excessively compressed, no valuable and hard mills have to be employed. When sintering for the second time, the temperature is higher and reaches between 1000 and 1300° C., but typically amounts to 1100° C., where a duration of 5–15 minutes, but typically 5 minutes is sufficient to obtain a desired thickness of the cap 5. This thickness is for example 0.7 mm, but depends upon the circumstances and the parameters, such as those of the dental restoration or crown, to be produced. The cap 5 can then be milled again, all be it with heavier and more accurate mills, for instance a diamond mill, to achieve the desired shape of the cap 5, which has for instance been determined based on the CAD/CAM programs by the computer.

In both part steps of sintering, such as it has been described hereinabove as an option, as well as with single direct sintering to obtain the final result of the cap 5, linear shrink plays only a relatively minor roll at the outer surface of the formed cap 5, because the ceramic material according to the present invention adheres to the top 2 of the underground 1 in connection with the "flow properties" of the glass component. This is the result of the considerable amount of glass component, which also results in a fast sintering process, especially in relation to the known oxidic ceramic powders, whether or not they comprise an added glass component.

As described above, the underground 1 is made from material, which is stable in a broad range of temperatures and oven proof, so that it maintains its shape during sintering. Therefore a good fit is ensured, whereby leaks along the edge of the restoration to be produced, further tooth decay and cavities under influence of bacteria are prevented. A specific advantage of the adhesion is, that the ceramic material according to the present invention forms a whole with the underground 1 and especially the top 2 thereof, whereby no pieces can break off the edges of the cap 5, particularly after the above mentioned optional first sintering step, whereafter the cap 5 is still fragile, awaiting complete compression in the optional second sintering step. When the sintering is performed in a single step, this aspect is less relevant.

Another considerable advantage of the ceramic material according to the present invention is, that color pigments can be added thereto, without disrupting the sintering process, because they have no influence on the sintering process, because of the "flow properties" of the glass component. When sintering the solid material, such as aluminum oxide or zirconium oxide, whether or not with the addition of a small amount of glass component, the color pigment could cause a disruption of the sintering process as a result, whereby the strength to be achieved of the cap 5 could worsen.

After forming the cap 5 the underground 1 can be removed in the manner described above by milling or dissolving at least the top 2 chemically, or alternatively by sandblasting.

The cap 5 can then be supplied as the basis for a dental restoration or a crown to a buyer, who will complete the crown, for instance by applying a structure of porcelain or ceramic in a dental laboratory. Preferably the combination of the underground 1 and the cap 5 on the top 2 is maintained in tact in order to apply on the cap 5 at least one and preferably more than one covering layer of porcelain, or an other material, that achieves a natural appearance of the dental restoration. The advantage thereof is that the foot 3 of the underground 1 can repeatedly be used to be placed in the clamps of a single or several different milling machines, while the entire crown or dental restoration is being completed. This is particularly the case when layers of porcelain or other ceramic material are applied on the cap 5 by sintering. These covering layers, which have been denoted in FIG. 2 by reference numbers 6 and 7, will have to be machined back to the dimensions determined with the measurements described above, of the geometry of the restoration to be produced.

Figure 2:
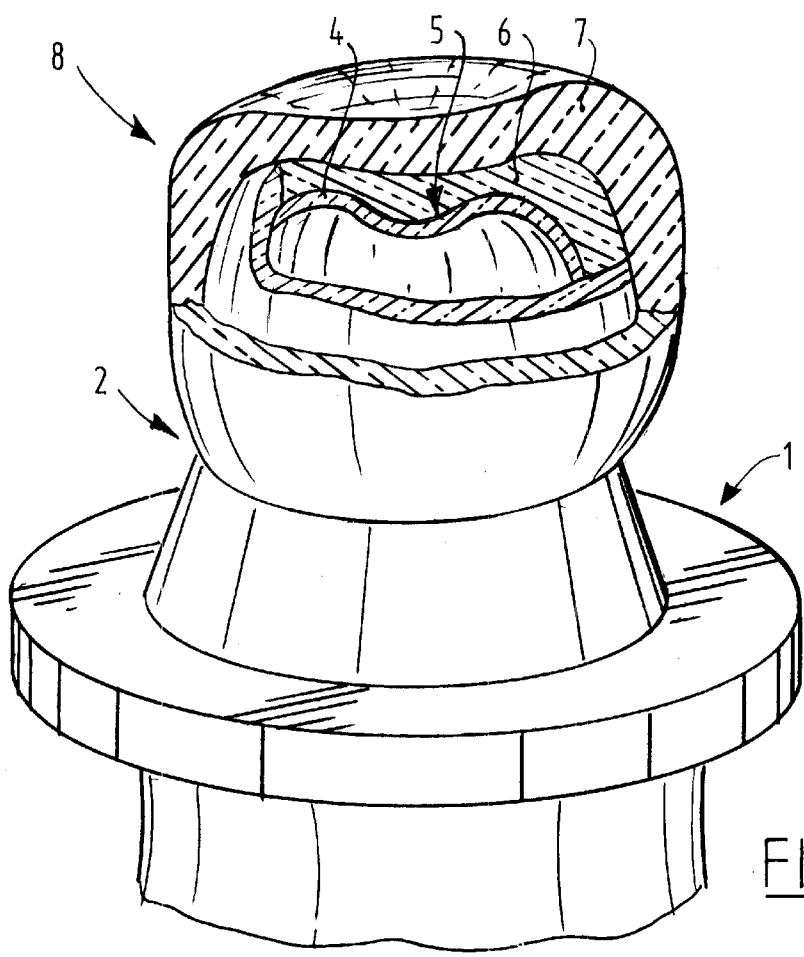
FIG. 2 shows, partially in section, a representation of a crown.

Because each of the covering layers 6 and 7 in FIG. 2 has separate properties in relation to especially color and transparency, a restoration with a very natural appearance can be obtained on a very strong basis, formed as cap 5, from ceramic material according to the present invention.

In the preferred embodiment shown in FIG. 2 of a restoration 8 to be produced, the underground 1 is still present in the end product of the restoration 8. The underground 1 and especially the foot 3 thereof is suitable to be placed in a clamp of a milling machine (not shown) in the different production steps of applying the separate layers in order to obtain the natural appearance of the restoration 8. As such a completely automated production process is possible, where for instance the dental laboratory, that is responsible for applying the cover layers 6 and 7 in order to obtain the eventual fit based on adjustment in situ of the generated computer simulations, has been supplied with the cap 5 on the top 2 of the underground 1. As an alternative the entire production process can take place at one manufacturer.

Applying the additional porcelain or ceramic layers on the basis 5 can also be achieved in an arbitrary manner and more than two separate cover layers with each properties of their own in relation to strength and color and transparency can be applied. In most cases two layers of porcelain will suffice to achieve an esthetic effect with a natural appearance.

A layer of porcelain, for instance the cover layer 6, adheres strongly to the cap 5 as a result of corresponding material properties of both components.

The last step in a method for producing a complete restoration 8 is coloring and glazing the outer surface thereof. This should be done based on dental properties of the patient. It is preferred, that the dental restoration or crown 8, as it is shown in FIG. 2, is heated. This should be done quickly, so that only the outer surface thereof is softened, in order to solidify again after cooling thereof. If desired pigment can be added to the softened outer surface of the dental restoration 8. Because of the short period, during which the restoration 8 is heated, where only a thin outer layer at the outer surface of the dental restoration 8 is softened, essentially no flow of material occurs, whereby the external shape is maintained. Polishing the restoration 8 is not strictly necessary.

Figure 3:
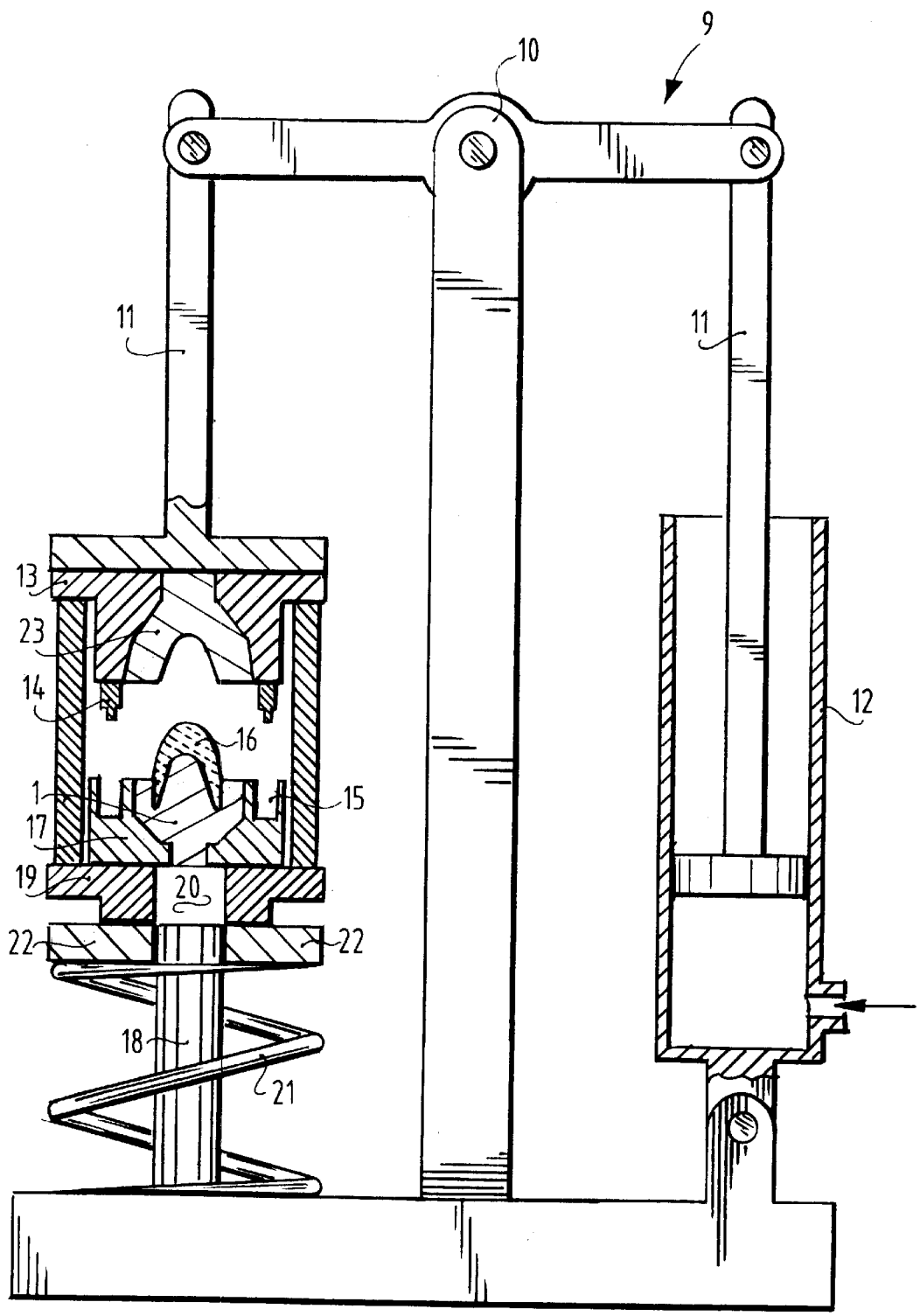
FIG. 3 shows a schematic view of a part of an apparatus for realizing a method according to the present application.

In FIG. 3 schematically an apparatus is shown for realizing the method of producing a basis from the ceramic material, that is the subject of the present invention, in connection with the other aspects of this invention.

FIG. 3 shows a press 9, comprising a lever 10 with arms 11 thereto. The right arm 11 forms a piston in a hydraulic cylinder 12 or a similar apparatus.

At the side opposite the cylinder 12 an underground 1 is placed, over which in the area of the protrusion, which is formed in correspondence with the tooth stump, a counter part, which is shaped as a top half 13, fits to press therebetween the basis into shape.

Pressing pins 14 extend downward into holes 15, whereby alignment of the top half 13 and the underground 1 is ensured, while pressing the ceramic material 16. During a downward stroke of the left arm 11 the bottom half 17 abuts the static pressure pen 18, whereby the bottom half 17 is pressed upward against the top half 13. For this a support 19 of the bottom half 17 is provided with a passage 20 with dimensions, corresponding to the pressure pen 18.

Forming the underground and a counterpart 23 is realized as follows.

First a wax model is made of the shape of the basis for the dental restoration to be produced. The bottom half 17 is placed on a glass plate and filled with an oven proof mass, from which the underground 1 must be formed. The material of this mass is 65% quartz, 8% aluminum oxide, 15% $NH_4H_2PO_4$ and 12% MgO, where this material is mixed with a colloidal solution of 30% $SiO_2$ in water. Before this material on the bottom half 17 will have had the opportunity to solidify, the wax cap is filled with the same material and placed on the bottom half 17 on the material, already present there. Subsequently the material is left to solidify during for instance 30 minutes. Thus an oven proof mass is formed, which is placed in the bottom half 17 of the apparatus shown in FIG. 3. Subsequently the clamp or press is closed, where the top half 13 is filled through a hole in the top thereof with the same ceramic material as that, which is described above and with which the bottom half 17 is filled to form the underground 1. Over the shape thus formed a adherence inhibiting material, such as grease is applied and the bottom half 17 with the underground therein is again placed in the press, shown in FIG. 3. Subsequently the press is closed, after which the top half 13 through a hole at the top side thereof is filled with the same ceramic material as the bottom half. The grease inhibits adherence of the top half and the bottom half to each other. The top half and the bottom half are separated from one another and burnt out, for instance during 20 minutes at a temperature of 1000° C., for instance in an atmospheric pre-heat oven.

Over the oven proof stump, which is formed in the underground 1, after cooling thereof ceramic material according to the present invention is applied and a cap is modelled thereover, which will serve as a basis for a dental restoration, to be formed subsequently.

The underground 1 with the ceramic material 16 thereon is heated, until it acquires a predetermined degree of consistency. Then the bottom half 17 with the underground 1 therein is placed in the press shown in FIG. 3 and the press is closed by actuating the cylinder 12. The halves of the press are accurately aligned as a result of the application of the fit pens 14 and the fit holes 15 and after forming the basis the underground can be removed, for instance by sand blasting, or using glass pearls.

Then the cap 5 or the basis is ready to be covered in further layers, for instance of porcelain, which are then baked thereon.

Below an example is described of the ceramic materials and a method for production thereof according to the present invention.

For each example twenty test bars were produced in accordance with ISO 6872.20. The test bars were tested in a universal pulling apparatus Zwick 1454, which was adjusted to a speed of 0.5 mm/min. Scanning Electron Microscopy research of the test bars proves, that zirconium oxide crystals are present in the glass phase thereof, which cause an enhancement of the strength.

The glass components were produced by melting the separate components described below and submerging them into water. Then the glass component was ground.

As for the zircon oxide preferably an Yttrium stabilized form is chosen. This form contains 6% Yttrium oxide, which shifts transformation of zircon oxide to a higher temperature.

The aluminum- and zircon oxide components were mixed in a tumbling mixer with the glass components. Subsequently the mixture is baked or sintered at a temperature of between 1100 and 1200° C., until the glass frit melts with the aluminum and/or zircon oxide to form a homogenous monolithic unit, such as a plate. The time, during which the mixture is sintered, is about 24 hours.

During this heat treatment a surface reaction takes place between the oxidic ceramic powders and the surrounding glass and a part of the oxidic phase diffuses, particularly aluminum oxide and/or zircon oxide, into the glass component. As a result of the composition of the glass, with diffusion products of the solid oxidic ceramics added thereto, crystals are formed in the glass component, which reinforce the glass component. After the sintering process the plate is removed from the oven and cooled in ambient temperatures during approximately 30 seconds, before it is submerged in water with a temperature of about 20° C. The material is subsequently ground during 8 hours to form a fine powder. This powder can be considered an intermediate product, from which a ceramic cap 5 for a dental restoration 8 can be produced.

In the subsequent examples the following glass components were used:

Glass component A has a composition, which corresponds closely to a glazing mass. This mass wets the aluminum oxide well.

Glass component B has a higher lithium oxide content than glass component A. This results in better wetting of the zircon oxide.

Glass component C wets the zirconium oxide even better than glass component B by an even higher lithium oxide content.

The following glass components (in percentage by weight) were produced from the following materials:

| Glass component | A | B | C |
|---|---|---|---|
| $SiO_2$ | 65 | 68 | 72 |
| $Al_2O_3$ | 14 | 7 | 2 |
| $K_2O$ | 9 | 6 | 3 |
| $Na_2O$ | 5 | 4 | 2 |
| BaO | 1 | 2 | 1 |
| $LiO_2$ | 3 | 10 | 18 |
| SrO | 1 | 1 | 1 |
| $B_2O_3$ | 1 | 1 | — |
| Remaining | 1 | 1 | 1 |

Composition in weight percentages of examples 1–6:

| Example | 1 | 2 | 3 | 4 | 5 | 6 |
|---|---|---|---|---|---|---|
| Glass component A | 40 | 40 | — | — | — | — |
| Glass component B | — | — | 40 | 40 | — | — |
| Glass component C | — | — | — | — | 40 | 40 |
| Aluminum oxide 1 m$\mu$ | 14 | 16 | 10 | 16 | 14 | 4 |
| Aluminum nioxide 5 m$\mu$ | 40 | 38 | 32 | 38 | 40 | — |
| Zirconium (Y-stab) 1 m$\mu$ | 4 | 4 | 4 | | | 16 |
| Zirconium (Y-stab) 5 m$\mu$ | | | 12 | 4 | 4 | 38 |
| Pigments | 2 | 2 | 2 | 2 | 2 | 2 |
| Bend strength, Mpa | 412 | 435 | 443 | 453 | 468 | 531 |
| Standard deviation, Mpa | 26 | 33 | 26 | 29 | 30 | 34 |
| Linear thermal expansion coefficient (measured in 20–500° C.) | 7,7 | 7,9 | 8,0 | 10,0 | 10,2 | 10,5 |

For examples 1–3 a porcelain mass was produced with a thermal expansion coefficient of 7.7 micrometer/m.K (measured between 20 and 500° C.). For examples 4–6 porcelain masses were used with an expansion coefficient of 10.0 micrometer/m.K (measured between 20 and 500° C.). These layers were cold pressed isostatically on the first layer, sintered at a temperature which was most suitable for the kind of porcelain actually used and during a similar time span, while a vacuum was being applied. The oven proof underground 1 was placed back into the automatic milling machine with ceramic layers thereon and milled back with diamond tools to dimensions, designed or determined by a computer. After completion of several milling or grinding processes on the cap 5 of the restoration 8 the oven proof material is removed by milling, sand blasting, or in the case of a chemically bound oven proof underground 1 through chemically dissolving the binding therein.

What is claimed is:

1. Method of producing a basis for a dental restoration to be applied at a place of use comprising:

(a) providing an underground with a shape corresponding to the place of use;

(b) providing a ceramic-based material, said ceramic-based material having a maximum density and surface, said ceramic-based material formed by mixing a ceramic material selected from the group of aluminum oxide, zirconium oxide, and titanium oxide, with a glass component to form a mixture;

(c) sintering said mixture of said ceramic material and said glass component whereby said glass component infiltrates said ceramic material and through a reaction at the surface of said ceramic material, acquires raw material of said ceramic material such that the glass is strengthened; and said ceramic material is sintered to a lower density than the maximum density thereof;

(d) grinding the sintered mixture into powder form;

(e) applying said powder onto said underground;

(f) further sintering said powder to provide a basis;

(g) machining the basis to the desired dimensions; and (h) repeating steps (f) and (g).

2. Method according to claim 1 wherein said sintering process of step (c) takes place in vacuum at a temperature of between approximately 750 and 1100° C. and during between approximately 1 and 12 minutes.

3. Method according to claim 1, wherein said sintering in step (f) takes place in vacuum at a temperature of between approximately 90 and 1500° C. during between approximately 2 and 12 minutes.

4. Method according to claim 1, wherein applying said powder onto said underground further includes:

spraying said powder using a carrier fluid onto said underground, and isostatically pressing said powder.

5. Method according to claim 1, wherein said applying said powder material comprises pressing said powder onto the underground using a counterpart thereby forming a cavity having the desired shape of the basis between the underground and the counterpart.

6. Method according to claim 5, where the underground and the counterpart are aligned during said pressing by at least one fit pin and one fit hole.

7. Method according to claim 1, further comprising removing the underground after applying said powder thereon.

8. Method according to claim 1, where the temperature during the step (c) sintering process is between approximately 1100° C. and 1200° C.

9. Method according to claim 1, where the step (c) sintering process occurs for 24 hours.

10. Method according to claim 1, comprising addition to said powder of at least one material selected from the group of metal oxides and pigments, after grinding and prior to applying said powder onto the underground.

11. Method according to claim 1, wherein said glass component comprises: 55–75 wt.-% $SiO_2$, 0.5–30 wt.-% $Al_2O_3$, 0.5–30 wt.-% $K_3O$, 0.5–15 wt.-% $Na_2O$ and 0.5–30 wt.-% $LiO_2$.

12. Method according to claim 11, wherein said glass component additionally comprises, in a lesser quantity than 5 wt.-% material, at least one of the compounds selected from the group of BaO, CaO, SrO, $La_2O_3$, $Sb_2O_3$, $TiO_2$, $F_2$, $B_2O_3$, ZnO, MgO and $CeO_2$.

13. Method according to claim 11, comprising melting the materials of said glass components to obtain glass; and grinding said glass in order to obtain said glass component for mixing with said ceramic based materials.

* * * * *